(12) United States Patent
Ossmann

(10) Patent No.: US 7,135,809 B2
(45) Date of Patent: Nov. 14, 2006

(54) ULTRASOUND TRANSDUCER

(75) Inventor: William J. Ossmann, Acton, MA (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 177 days.

(21) Appl. No.: 09/919,232

(22) Filed: Jul. 31, 2001

(65) Prior Publication Data

US 2003/0011285 A1    Jan. 16, 2003

Related U.S. Application Data

(60) Provisional application No. 60/301,282, filed on Jun. 27, 2001.

(51) Int. Cl.
*H01L 41/08* (2006.01)

(52) U.S. Cl. .................. 310/335; 310/334; 128/662.03

(58) Field of Classification Search ........ 310/334–337, 310/344
See application file for complete search history.

(56) References Cited

U.S. PATENT DOCUMENTS

| | | | | |
|---|---|---|---|---|
| 4,097,835 A | * | 6/1978 | Green | 340/1 R |
| 4,211,949 A | * | 7/1980 | Brisken et al. | 310/322 |
| 4,217,516 A | * | 8/1980 | Iinuma et al. | 310/335 |
| 4,644,214 A | * | 2/1987 | Takamizawa et al. | 310/334 |
| 4,865,042 A | * | 9/1989 | Umemura et al. | 128/660.03 |
| 4,957,100 A | * | 9/1990 | Herzog et al | 128/24 A |
| 5,083,568 A | * | 1/1992 | Shimazaki et al | 128/662.03 |
| 5,103,129 A | * | 4/1992 | Slayton et al | 310/335 |
| 5,186,175 A | * | 2/1993 | Hirama et al. | 600/447 |
| 5,293,351 A | | 3/1994 | Noponen | 367/7 |
| 5,483,963 A | | 1/1996 | Butler et al. | 128/661.01 |
| 5,552,004 A | * | 9/1996 | Lorraine et al | 156/154 |
| 5,711,058 A | * | 1/1998 | Frey | 29/25.35 |
| 5,820,564 A | | 10/1998 | Slayton et al. | 600/459 |
| 5,922,962 A | * | 7/1999 | Ishrak et al | 73/632 |
| 6,104,126 A | * | 8/2000 | Gilmore | 310/334 |
| 6,139,496 A | | 10/2000 | Chen et al. | 600/437 |
| 6,153,967 A | * | 11/2000 | Kobayashi et al | 310/334 |
| 6,396,199 B1 | * | 5/2002 | Douglas et al. | 310/335 |

FOREIGN PATENT DOCUMENTS

DE    3219229 A1    11/1983
EP    0713102 A1    5/1996

* cited by examiner

*Primary Examiner*—Mark Budd

(57) ABSTRACT

Acoustic imaging systems are provided. A preferred system includes a protective cover configured to mate with a transducer body. The transducer includes a two-dimensional transducer element matrix array formed by a plurality of individually controllable transducer elements. The protective cover is superposed above the two-dimensional matrix array and is transparent to incident acoustic energy. Preferably, the protective cover is shaped to reduce patient discomfort and repetitive motion injuries to sonographers. Alternative embodiments comprise a shaped two-dimensional transducer element matrix array. Methods for improved ultrasound imaging are also provided.

11 Claims, 10 Drawing Sheets

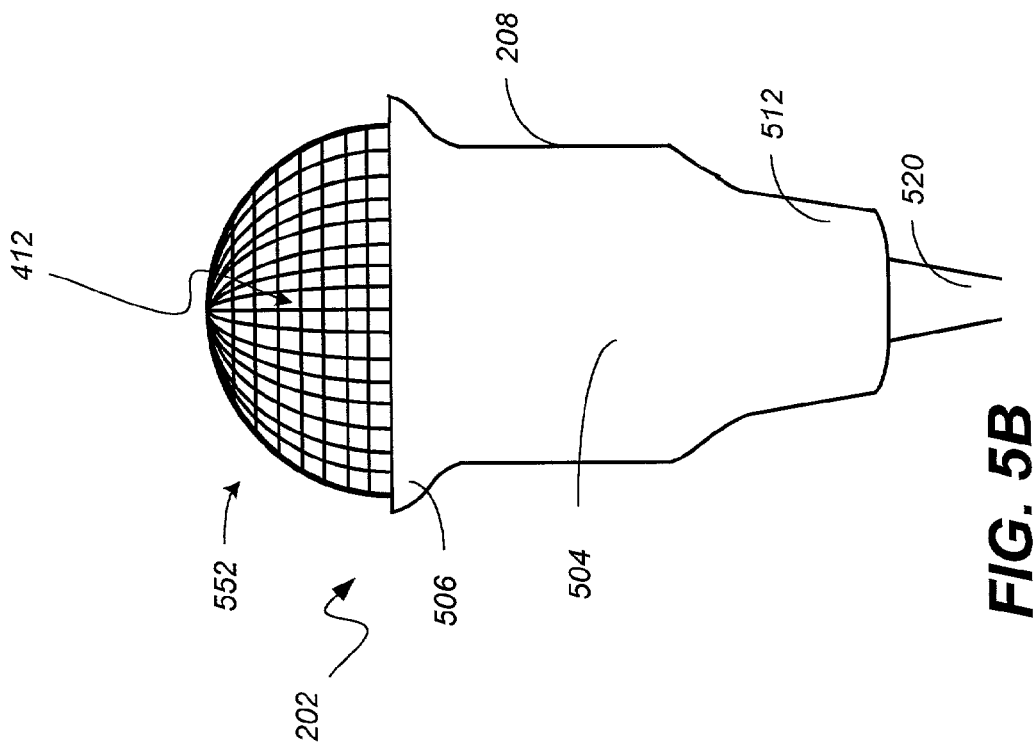
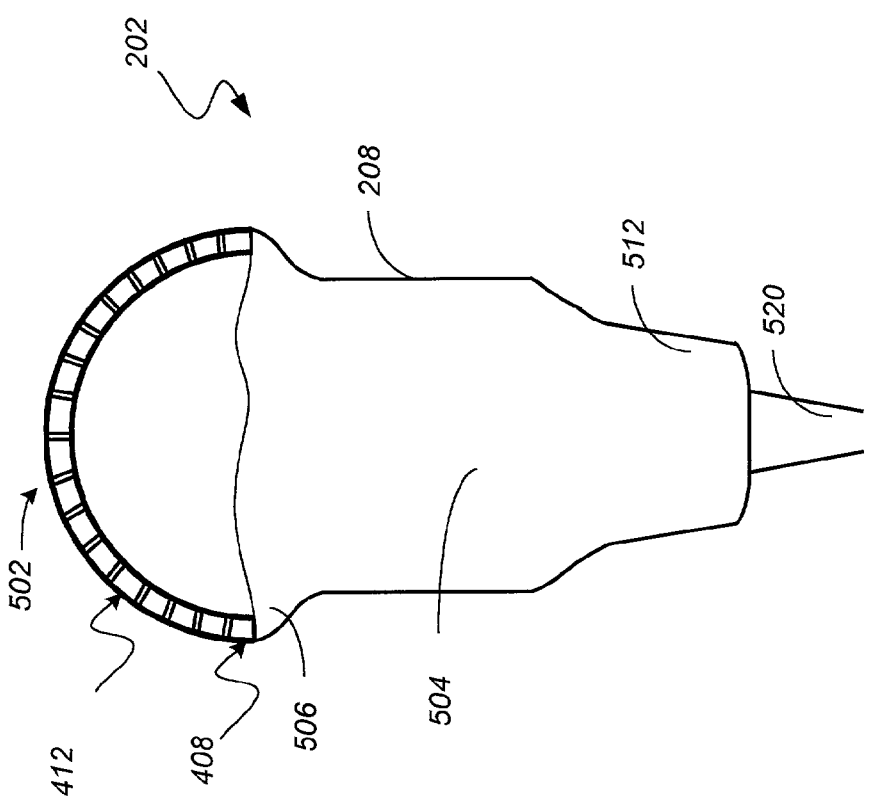
FIG. 5B
FIG. 5A

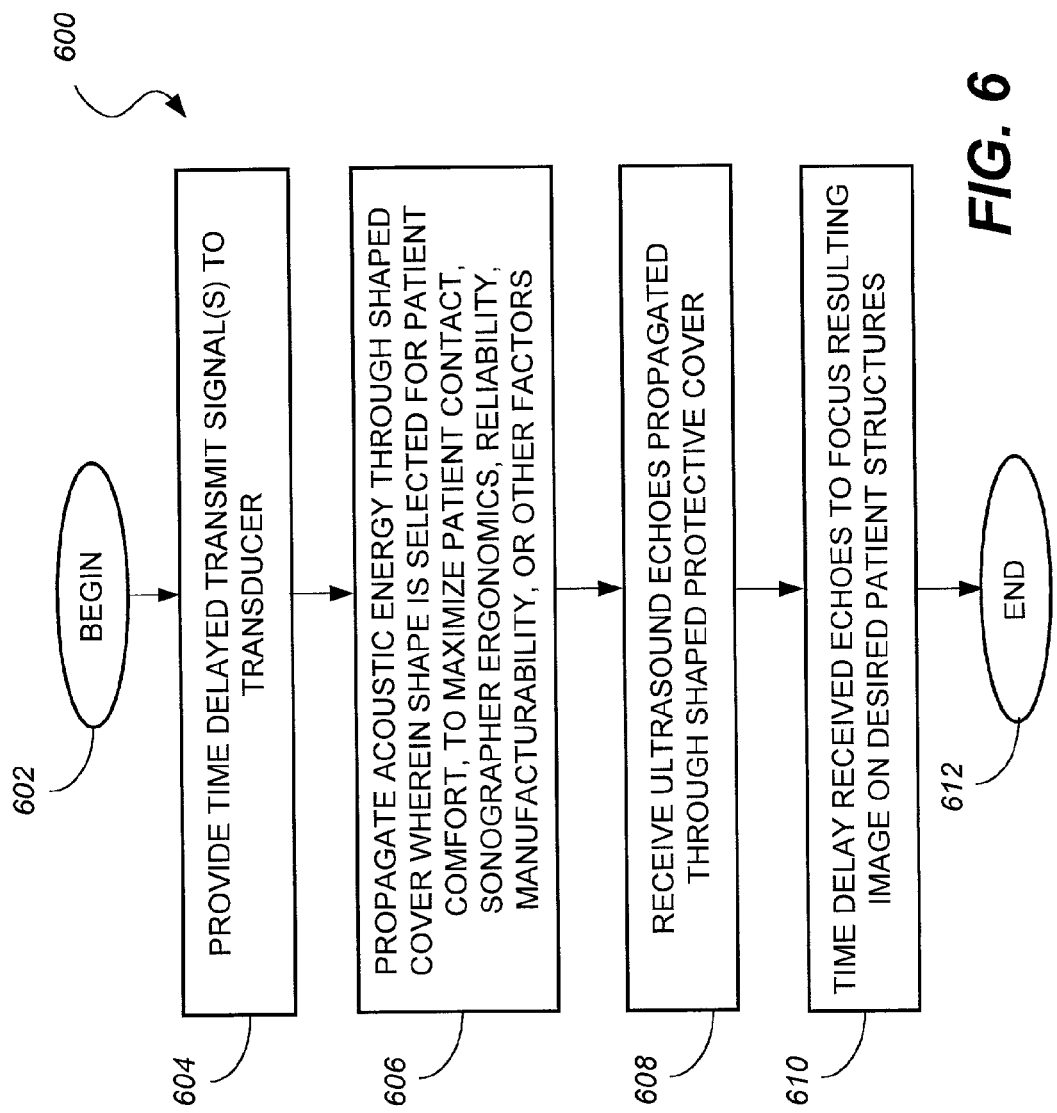

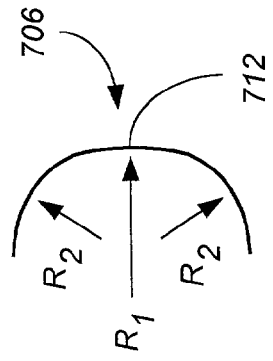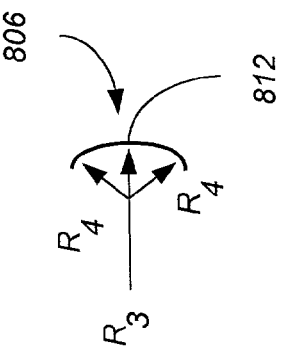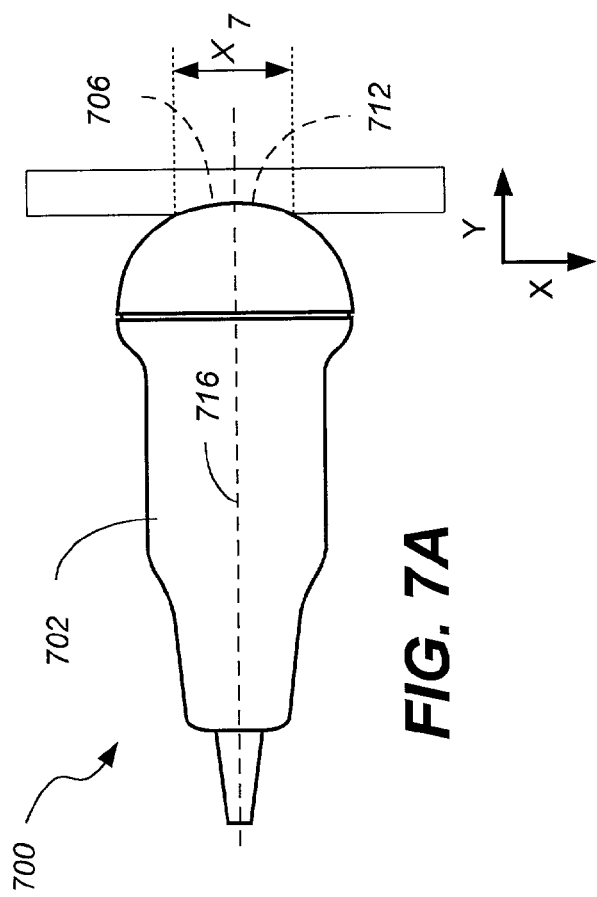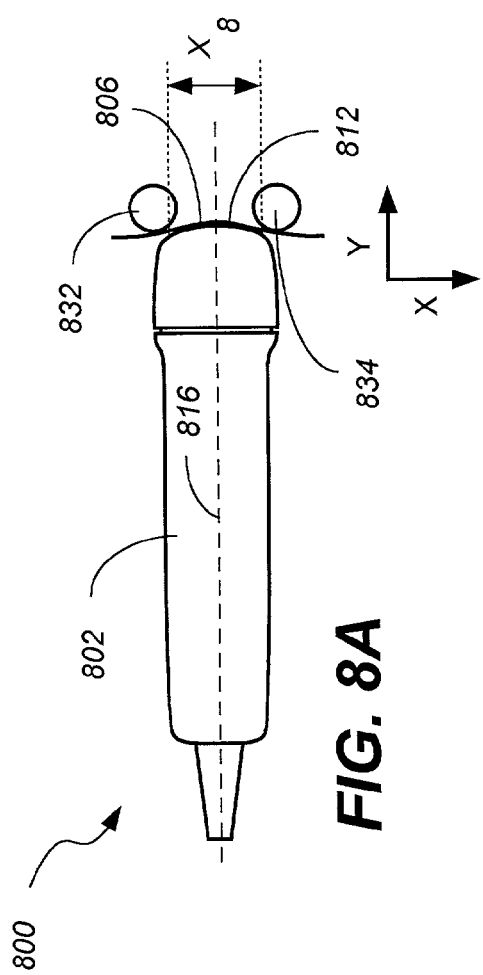

ULTRASOUND TRANSDUCER

CROSS-REFERENCE TO RELATED APPLICATION

This application claims priority to copending U.S. provisional application entitled, "IMPROVED ULTRASOUND TRANSDUCER" having Ser. No. 60/301,282, filed Jun. 27, 2001, which is entirely incorporated herein by reference.

TECHNICAL FIELD

The present application generally relates to acoustic imaging. More particularly, the application relates to ultrasonic imaging systems and methods that use transducers with two-dimensional transducer element arrays.

BACKGROUND

Ultrasound imaging systems have become an important diagnostic tool in many medical specialties. One important advantage of an ultrasound imaging system is real-time scanning. For example, an ultrasound imaging system can produce images so rapidly that a sonographer can scan internal organs or can discern motion within a body, such as blood flow, with real-time, interactive, visual feedback. This allows the sonographer to examine structures of interest and to modify the examination in real-time, thereby improving both diagnostic quality and patient throughput.

Along with the advantages of real-time, interactive, visual feedback, sonographers are still concerned with system resolution. In an ultrasound imaging system, system resolution depends on the system's ability to focus. The ability to focus depends, in turn, on the effective aperture of a transducer element array in a probe associated with the ultrasound imaging system. Currently two types of arrangements of transducer array elements are used for real-time, ultrasound imaging systems.

One arrangement comprises a single transducer element or an annular array of transducer elements. Ultrasound imaging systems using this arrangement of transducer array elements rely on mechanical motion of the probe to sweep an acoustic beam over a region of interest.

A second arrangement of transducer array elements comprises an array of transducer elements which is activated by electronic circuits which produce electronically induced time delays in the transducer element acoustic outputs. These time delays induce measurable phase delays, which cause the acoustic beam produced by the transducer element array to be steered and/or focused.

Links between electronic circuits which generate transmit pulses for transducer array elements and the transducer array elements that receive the transmit pulses are referred to as beamformer channels. Electronic steering and/or focusing of an acoustic beam produced by the transducer element array is achieved by electronically delaying transmit pulses, on a beamformer channel-by-beamformer channel basis, to create an effective protective cover having varying thickness.

Due to limits on: (a) the size and complexity of a cable connecting the ultrasound probe with the processing system and (b) the number of beamformer channels available in a reasonably priced ultrasound system, electronic focusing has been limited to a lateral direction (a direction parallel to the imaging plane). Focusing in an elevation direction (a direction perpendicular to the imaging plane) has been accomplished by placing a mechanical lens, of fixed curvature, on the probe face.

Conventional modifications in elevation focusing have been accomplished by changing the probe aperture and/or the properties of the mechanical lens. Although it is known that changing frequency can change focal depth (higher frequencies producing deeper focusing than lower frequencies), it is not considered advantageous to change frequency to change focal depth because higher frequencies are attenuated more rapidly in tissue than lower frequencies.

Consequently, it is known that in order to change elevation focusing of a transducer element array, one ought to change the elevation aperture and/or change the effective curvature of a lens associated with the transducer element array. For example, in imaging a deep organ, the lens ought to have a large aperture and mild curvature and, in imaging a shallower object, the lens ought to have a smaller aperture and a tighter curvature.

As is known, transducer array elements in an ultrasound probe can be arranged in a one-dimensional (1-D) array, a one-and-a-half-dimensional (1.5-D) array, or a two-dimensional (2-D) array (the size of a typical 1-D transducer array element is on the order of 0.5 wavelengths in the lateral direction and is on the order of 50 wavelengths in the elevation direction). In a 1-D array, transducer elements are generally disposed in the lateral direction, with a single row of elements in the elevation direction. Conventional phase linear arrays and curved arrays are generally considered 1-D transducer element arrays.

In a 1.5-D array, transducer elements are mounted in both the lateral and elevation directions, but control and data electrical connections are symmetrically connected about the elevation center so that an acoustic beam produced by a 1.5-D array can only be steered in the lateral direction. In a 2-D array, transducer elements are arranged in both the lateral and elevation directions, with electrical connections providing both transmit/receive control and excitation signals to transducer elements arranged in both directions. An acoustic beam produced by a 2-D array can be steered and focused in two dimensions. An example of a 2-D array ultrasound probe can be found in U.S. Pat. No. 5,186,175.

The advantages of 2-D array imaging are well known. For example, such advantages include the ability to electronically steer in two (2) dimensions (i.e., both lateral and elevation), enhanced resolution due to improved elevation focusing, and improved phase aberration correction through refined comparison of propagation velocities. The flexibility and enhanced resolution associated with 2-D transducers has eliminated the need for an acoustic lens shaped to mechanically focus the acoustic beams. However, the transducer elements still need to be protected. Consequently, the faces of 2-D transducers are configured with a relatively flat acoustically transparent material layer.

Sonographers can obtain images of a region within a body by properly positioning an ultrasound transducer against the body. In order to obtain images having diagnostic value, the sonographer may have to manipulate the position of the probe by sliding, rotating, and/or tilting the probe with respect to the patient.

A flat transducer face, such as those used with 2-D transducers, degrades image quality because it provides poorer contact with the body structures of a patient than a transducer with a curved surface. More specifically, a flat transducer surface causes spurious reflections and block portions of the acoustic aperture. Another disadvantage associated with a transducer configured with a flat face is that such transducers either have sharp edges, which can cause patient discomfort, or the transducers have an overly broad footprint to permit rounder edges.

Transducers configured with an overly broad footprint further impair contact between the transducer face and the patient, which can cause a sonographer to apply greater pressure along the longitudinal axis of the transducer in an attempt to improve contact between the transducer face and the patient. The increase in sonographer induced pressure can result in patient discomfort, as well as repetitive motion injuries to the sonographer. One area where maintaining appropriate contact between the transducer face and the patient is particularly problematic is intercostal cardiac and thoracic imaging. Generally, for these applications, the transducer housing contains a 2-D array of transducer elements selected for the expected enhanced resolution due to improved elevation focusing.

Consequently, there is a need for an improved transducer that addresses these and/or other shortcomings associated with conventional transducers.

SUMMARY

Embodiments of the improved ultrasound transducer may be construed as providing acoustic imaging systems. In a preferred embodiment, the system includes a shaped protective cover configured to mate with a transducer body. The protective cover is formed, at least partially, of a material, which exhibits acoustic properties that redirect ultrasound energy passing through the material into the body to be imaged. The shaped protective cover provides patient comfort, an increased acoustical window, and reduces the incidence of repetitive motion injuries to sonographers. An ultrasound imaging system configured with the improved transducer electronically focuses acoustic energy that traverses the protective cover.

Other embodiments of the present invention may be construed as providing methods for acoustically imaging a patient, for example. A preferred method includes the steps of: (1) providing a transducer having a shaped protective cover formed, at least partially, of an acoustic focusing material; (2) propagating acoustic waves from the protective cover; (3) receiving acoustic waves reflected from structures within the body to be imaged; (4) converting said received acoustic waves to electrical signals; and (5) processing said electrical signals to produce an image.

Other systems, methods, and features, of the improved ultrasound transducer will be apparent to one skilled in the art upon examination of the following drawings and detailed description. It is intended that all such additional systems, methods, and features are included within this description, are within the scope of the improved ultrasound transducer, and protected by the accompanying claims.

BRIEF DESCRIPTION OF THE DRAWINGS

The improved ultrasound transducer can be better understood with reference to the following drawings. The components in the drawings are not necessarily to scale; emphasis instead is placed upon clearly illustrating the principles of the transducer. Moreover, in the drawings, like reference numerals designate corresponding parts throughout the several views.

FIG. 5A is a partial cross-sectional side view illustrating an embodiment of the improved ultrasound transducer of FIG. 2.

FIG. 5B is a side view illustrating another embodiment of the improved ultrasound transducer of FIG. 2.

FIG. 6 is a flowchart depicting preferred functionality of the imaging system of FIG. 2.

FIG. 7A is a plan view of an alternative embodiment of the present invention.

FIG. 7B is a schematic diagram depicting detail of the protective cover of FIG. 7A.

FIG. 8A is a plan view of an alternative embodiment of the improved ultrasound transducer.

FIG. 8B is a schematic diagram depicting detail of the protective cover of FIG. 8A.

DETAILED DESCRIPTION

Conventional one-dimensional (1-D) phased array transducers utilized for ultrasonic imaging typically incorporate lenses that focus acoustic beams transmitted from the transducers. In particular, the mechanical configuration of such a lens typically is selected to focus an acoustic beam from a transducer in an elevation dimension. The elevation dimension also may be focused mechanically, such as by implementing a concave shape at the array of the transducer. The lateral dimension typically is focused electronically.

By way of example, a conventional 1-D phased array transducer uses a lens that promotes focusing of transmitted acoustic energy within a body, e.g., a human body. Oftentimes, the material of such a lens possesses an acoustic velocity that is less than that of the human body (approximately 1.5 mm/$\mu$sec). So provided, the acoustic energy propagated into the body by the ultrasound transducer through the acoustic lens tends to converge or focus within the body. Focusing of acoustic energy transmitted from a conventional 1-D transducer within a body is depicted schematically in FIG. 1.

Figure 1:
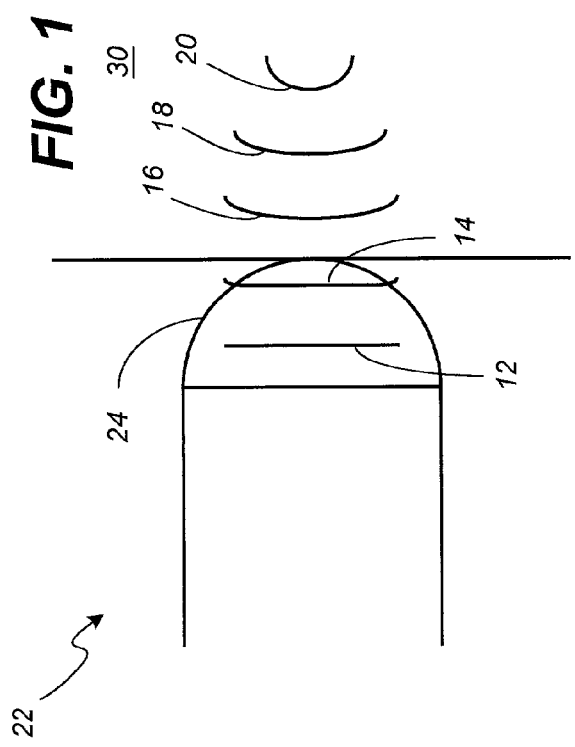
FIG. 1 is a schematic diagram depicting a conventional 1-D transducer transmitting acoustic energy into a representative body.

In FIG. 1, representative acoustic waves 12, 14, 16, 18, and 20 are shown being transmitted from transducer 22 via a focusing lens 24. As depicted therein, the acoustic waves tend to focus as they propagate deeper into body 30 due, at least in part, to the material of the lens 24.

As is known, acoustic energy propagates at various velocities and with various wave-front shapes depending upon, for example, the acoustic velocity and acoustic impedance of a material(s) through which the acoustic energy is propagated. For instance, the closer the acoustic velocity of a lens material is to that of the body, the closer the energy is transmitted from a transducer and into the body at the incident angle. Additionally, the closer the acoustic impedance of the lens material is to that of the body, more ultrasonic energy is transmitted from the transducer and into the body.

Figure 2:
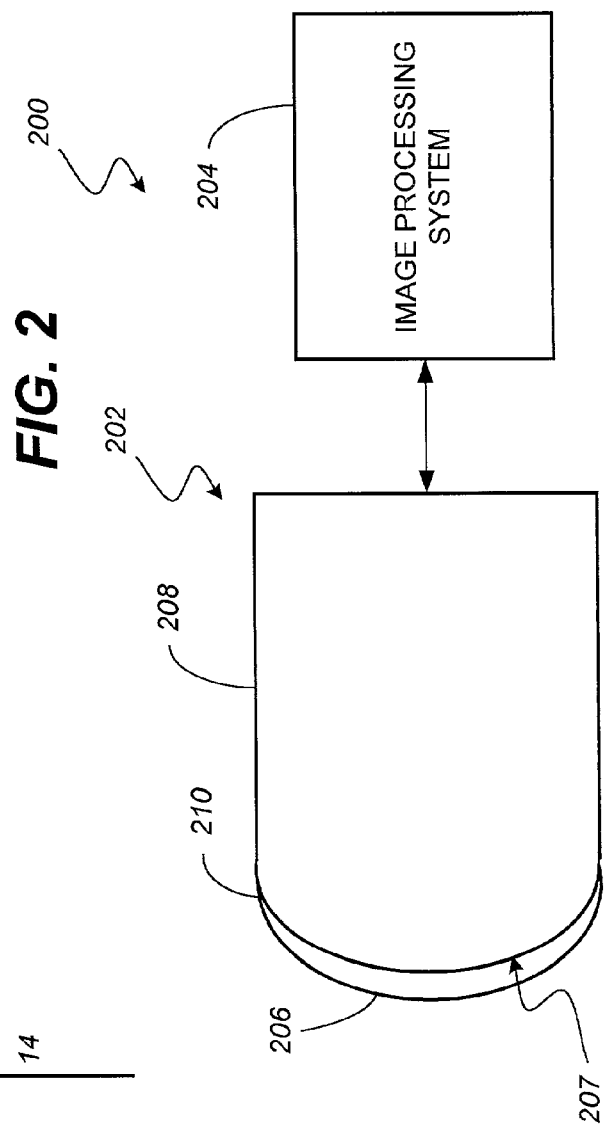
FIG. 2 is a schematic diagram depicting the improved ultrasound transducer in association with an image processing system.

As shown in FIG. 2, a preferred embodiment 200 of the imaging system incorporates a transducer probe ("transducer") 202. By way of example, transducer 202 can be a two-dimensional (2-D) phased array transducer. Transducer 202 is electrically coupled with an image processing system 204. Image processing system 204 provides various signals to transducer 202 so as to enable the transducer 202 to transmit acoustic energy via a plurality of transducer elements arranged in a 2-D array about a transducer face 207. The transmitted acoustic energy as well as reflected acoustic echoes may then traverse a protective cover 206 manufactured from an acoustically transparent material. The transducer 202 converts the reflected acoustic echoes into electrical signals that are returned to the image processing system.

Protective cover 206 is maintained in position relative to the transducer body 208 by a nose portion 210 of the transducer body 208. In particular, protective cover 206 is adapted to seat at least partially within an aperture (not shown) defined by the nose portion 210. Various other configurations, however, can be used.

In prior art transducers, protective cover 206 is configured as an acoustically non-focusing lens. More specifically, protective cover 206 is formed of selected material(s) and/or exhibits a particular shape that enables acoustic energy to be propagated into a body, e.g., a human body, without substantially mechanically focusing the acoustic energy. By way of example, prior art embodiments of the ultrasound transducer 200 may include a protective cover 206 that is at least partially formed of an acoustic-matching material. Such an acoustic-matching material preferably exhibits an acoustic velocity and impedance that substantially match the acoustic velocity and acoustic impedance of a typical body.

In alternative prior art embodiments, non-focusing is achieved by making the transducer face 207 flat or convexly curved and maintaining a uniform thickness in that part of the protective cover 206 that lies in the acoustic path. For instance, a material exhibiting an acoustic velocity within the range of approximately 1.4 mm/µsec to approximately 1.6 mm/µsec could be considered an acoustic-matching material for medical diagnostic applications. An acoustic-matching material also preferably exhibits an acoustic impedance within the range of approximately 1.3MRayl to approximately 1.7MRayl.

In some embodiments, the acoustically non-focusing protective cover 206 may be formed of butadiene, styrene butadiene, and/or an associated classes of rubbers and/or polymers, among others. These materials typically attenuate acoustic energy at approximately 3 dB/cm at 2 MHz and approximately 8 dB/cm at 5 MHz. As is known, conventional lens materials, such as silicone, attenuate acoustic energy at approximately 9 dB/cm at 2 MHz and approximately 33 dB/cm at 5 MHz.

It should be noted that one of ordinary skill in the art may choose to provide a protective cover 206 formed of materials that, individually, may not be considered acoustic-matching materials. However, providing a combination of materials that together exhibit acoustic-matching properties, e.g., an acoustic velocity within the range of approximately 1.4 mm/µsec to approximately 1.6 mm/µsec and an acoustic impedance within the range of approximately 1.3MRayl to approximately 1.7MRayl, is considered for the improved ultrasound transducer.

By providing an acoustically non-focusing protective cover 206, imaging system 200 may enable transmission of acoustic energy into a patient's body that is suitable for electronic focusing in both the lateral and elevational dimensions. In particular, the imaging system 200 may provide acoustic beams that are conducive to comparatively sensitive electronic focusing. This could facilitate improved zoom imaging functionality as compared to other ultrasound imaging systems, which use mechanically focused lenses. It also is presumed that an imaging system using an acoustically non-focusing protective cover 206 may provide acoustic beams that are particularly well suited for contrast imaging applications. As described in detail hereinafter, improved imaging systems can include various shapes of protective covers 206, which are at least partially formed of acoustic-matching material.

A disadvantage of the prior art is that the use of a non-focusing protective cover 206 may be undesirable. A suitable acoustic-matching material that meets other transducer requirements such as durability, chemical resistance, and biocompatibility may not be available or may require excessive development effort. Furthermore, requirements for maintaining contact between the transducer 202 and the patient may dictate a shape for the protective cover surface that causes substantial focusing of the acoustic energy. The improved ultrasound transducer 202 advances the art of ultrasound imaging by electronically compensating for the focusing characteristics of the protective cover 206.

Figure 3:
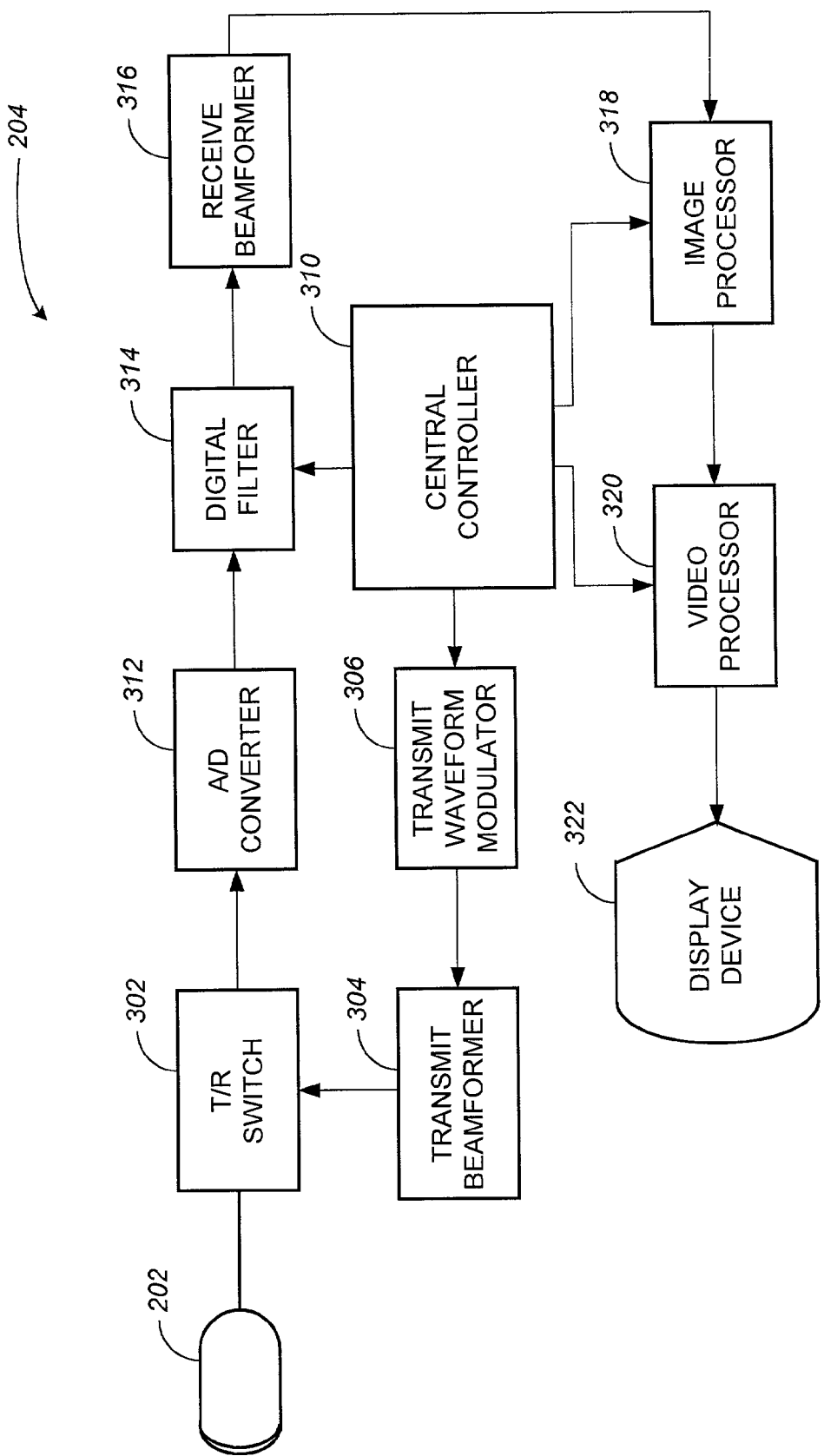
FIG. 3 is a schematic diagram of the improved ultrasound transducer of FIG. 2 showing detail of the image processing system.

Referring now to FIG. 3, a preferred embodiment of the imaging processing system 204, will be described in detail. It will be appreciated that FIG. 3 does not necessarily illustrate every component of the preferred system, emphasis instead being placed upon the components most relevant to the systems and/or methods disclosed herein.

As depicted in FIG. 3, image processing system 204 includes the improved transducer 202, which is electrically connected to a T/R switch 302 of the image processing system 204. T/R switch 302 places the transducer 202 in either a transmit or receive mode. In order to facilitate transmission of acoustic energy via the transducer 202 during operation in the transmit mode, image processing system 204 includes a transmit beamformer 304 that sets the transmit frequency, $f_o$, and magnitude of various transmit signals. The transmit beamformer 304 is in communication with a transmit waveform modulator 306 that generates the various transmitted signal lines. As illustrated in FIG. 3, the transmit beamformer 304 and transmit waveform modulator 306 operate under control of a central controller 310.

In order to facilitate reception of acoustic energy via the transducer 202 during operation in the receive mode, the image processing system 204 includes an A/D converter 312, which converts analog signals received from the transducer 202 into digital signals. A digital filter 314, e.g., an RF filter, filters signals outside a desired receive band from the received data. Next, a receive beamformer 316 receives the filtered digital signals representing the received ultrasound echoes.

The receive beamformer 316 may be designed to receive multiple digital echo waveforms (corresponding with a plurality of sets of transducer elements from the 2-D array of transducer elements) from the A/D converter 314. The receive beamformer 316 may combine the multiple digitized echo waveforms to form a single acoustic line. To accomplish this task, a plurality of parallel processing channels within the receive beamformer 316 may delay the separate echo waveforms by different amounts of time and then may add the delayed waveforms together, in order to create a composite digital acoustic line. Furthermore, the receive beamformer 316 may receive a series of data collections for separate acoustic lines in succession over time and process the data in a pipeline-processing manner.

An image processor 318 may contain a suitable species of random access memory (RAM) and may be configured to receive a series of composite digital acoustic lines from the receive beamformer 316. The acoustic lines can be defined within a three-dimensional coordinate space. The image processor 318 may be configured to mathematically manipulate image information within the received and filtered digital acoustic lines. In addition, the image processor 318 may be configured to accumulate acoustic lines of data over time for signal manipulation. In this regard, the image processor 318 may further include a scan converter to convert the data as stored in the RAM in order to produce pixels for display. Each scan converter may process the data in the RAM once an entire data frame (i.e., a set of all acoustic lines in a single view, or image/picture to be displayed) has been accumulated by the RAM.

For example, if the received data is stored in RAM using polar coordinates to define the relative location of the echo information, the scan converter may convert the polar coordinate data into rectangular (orthogonal) data capable of being raster scanned via a raster scan capable processor. The ultrasound imaging system 204, having completed the receiving, echo recovery, and image processing functions, to form a plurality of image frames associated with the plurality of ultrasound image planes, may forward the echo image data information to a video processor 320 as illustrated in FIG. 3.

Video processor 320 may be designed to receive the echo image data information and may be configured to raster scan the image information. The video processor 320 produces picture elements (i.e., pixels) that may be forwarded to the display device 322. In addition, the picture elements may be forwarded to a video memory device (not shown). Video memory devices may include a digital videodisc (DVD) player/recorder, a compact disc (CD) player/recorder, a video cassette recorder (VCR), or other video information storage device. As is known in the art, these video memory devices permit viewing and or post data collection image processing by a user/operator in other than real-time.

As further illustrated in FIG. 3, display device 322 may be configured to receive the picture elements (i.e., the pixel data) from the video processor 320 and drive a suitable display screen or other imaging device (e.g., a printer/plotter) for viewing of the ultrasound images.

Many variations of the image processing system 204 presented in FIG. 3 may be operational with the improved ultrasound transducer 202. For example, the receive beamformer 316 may be split into two parts, an analog portion being between the T/R switch 302 and the AID converter 312 (not shown) and a digital portion disposed after the digital filter 314 as illustrated in FIG. 3.

Figure 4:
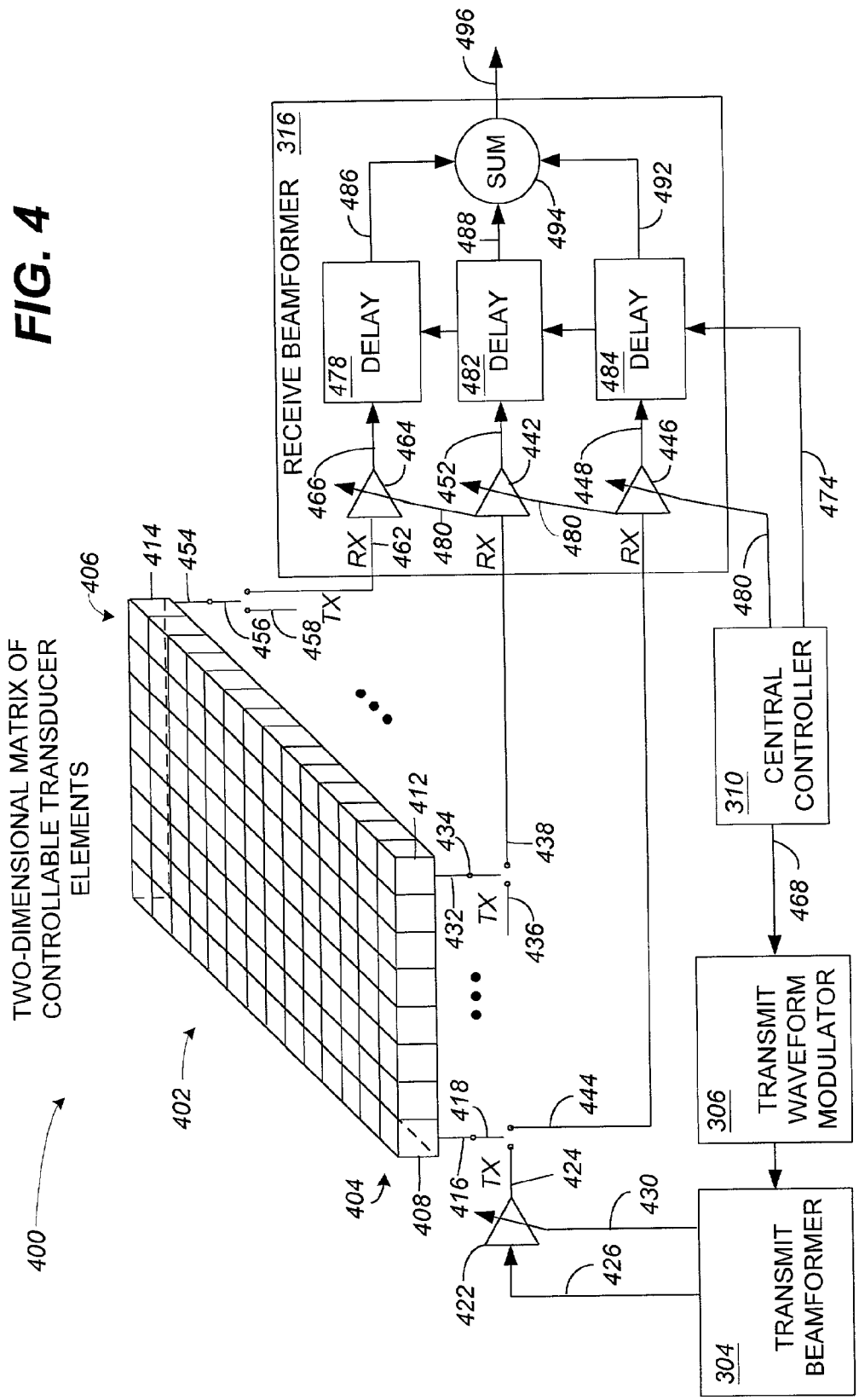
FIG. 4 is a schematic diagram illustrating control of the transducer elements of the improved ultrasound transducer of FIG. 2.

Reference is now directed to FIG. 4, which presents a schematic view illustrating a transducer control system 400. The transducer control system 400 controls a two-dimensional transducer element array 402. The two-dimensional transducer element array 402 includes a plurality of ultrasonic transducer elements, exemplar ones of which are illustrated using reference numerals 408, 412 and 414. The ultrasonic transducer elements 408, 412 and 414 are arranged in rows and columns, exemplar ones of which are illustrated using reference numerals 404 and 406, respectively. Such a configuration is sometimes referred to as a matrix array. However, other transducer element configurations are possible.

Although the schematic of FIG. 4, illustrates a planar 8×14 array of ultrasonic transducer elements, it should be mentioned that the concepts of the invention are applicable to any two-dimensional ultrasonic transducer element array configuration, including configurations in which ultrasonic transducer elements are curved in one or both of the two dimensions. For example, two-dimensional transducer element arrays having cylindrical, spherical, toroidal, or other curved surfaces are possible and may use slightly modified beamforming than that associated with the planar two-dimensional transducer element array 402 illustrated in FIG. 4.

Each of the elements 408, 412 and 414 of the two-dimensional transducer element array 400 is individually controllable. Specifically, each of the transducer elements 408, 412 and 414 can function as a transmit element and as a receive element, and each receives individualized control signals. For example, ultrasonic transducer element 408 is electrically coupled via connection 416 to a transmit/receive (T/R) switch 418. The T/R switch 418 is controlled by a signal (not shown) from the central controller 310 to permit the transducer element 408 to function in a transmit mode and in a receive mode.

When the transducer element 408 is used in a transmit mode, the transducer element 408 receives a transmit pulse from the transmit beamformer 304 through connection 426 and via the variable amplifier 422 via connection 424. The variable amplifier 422 is used to define the characteristics of the transmit pulse applied to the transducer element 408 and is controlled by amplitude controller 420 via connection 430. Although omitted for simplicity, each element in the two-dimensional transducer element array 402 includes a similarly controlled variable amplifier.

When the transducer element 408 is used in a receive mode, ultrasonic energy that impinges upon the surface of the transducer element 408 is converted to an electrical signal. The electrical signal is communicated via connection 416, through T/R switch 418 (which is now connected to connection 444 by operation of a control signal from the central controller 310) so that the receive signal is applied to variable gain amplifier 446. The variable gain amplifier 446 amplifies the electrical receive signal and supplies the signal over connection 448 to delay element 484.

In a similar manner, the transducer element 412 receives a transmit pulse via connection 436 and supplies a receive signal via connection 438 to variable gain amplifier 442. Variable gain amplifier 442 supplies the received signal via connection 458 to delay element 482. Similarly, transducer element 414 receives a transmit signal via connection 458, through switch 456 and connection 454, while the receive signal is passed via connection 454, through switch 456 and connection 462 to variable gain amplifier 464. The variable gain amplifier 464 supplies the amplified receive signal on connection 466 to the delay element 478. Each element in the two-dimensional transducer element array 402 is thus controlled, thereby allowing full control over each element in the two-dimensional transducer element array 402.

The variable gain amplifiers 462, 442 and 446, and the delay elements 478, 482 and 484 are all contained within receive beamformer 316. While shown as having only three variable gain amplifiers and three delay elements, the receive beamformer 316 includes sufficient amplifiers and delay element circuitry (and other processing circuitry) for each of the transducer elements in the two-dimensional transducer element array 402. Furthermore, various multiplexing, sub-beamforming, and other signal processing techniques can be performed by the receive beamformer 316. However, for simplicity of illustration, the receive beamformer 316 in FIG. 2 includes only three delay elements. Each of the amplifiers in the receive beamformer 316 is controlled by a signal via connection 480 from the central controller 310. The signal on connection 480 determines the receive gain applied by each of the variable gain amplifiers 464, 442 and 446. The gain applied by each of the amplifiers may vary. Similarly, each delay element 478, 482 and 484 is operated by a signal from the central controller 310 via connection 474. This control signal determines the amount of delay that each of the delay elements 478, 482, and 484 applies to their respective receive signals. In this manner, the receive aperture can be controlled with a high degree of precision, because each transducer element in the two-dimensional transducer element array 402 includes a respective variable gain amplifier 442, 446 and 464 and control circuitry.

The output of delay elements 478, 482, and 484 are respectively supplied via connections 486, 488 and 492 to summing element 494. Summing element 494 combines the output of each delay element and supplies a beamformed signal on connection 496 to additional processing elements, such as the image processor 318 (not shown). In alternative configurations, the variable gain amplifiers 464, 442 and 446 may be located after the delay elements 478, 482, and 484, respectively. Further, the outputs of the delay elements 478, 482, and 484 may be combined into sub-arrays and variable gains may be applied to each sub-array either before or after the sub-array signal passes through its respective delay prior to the summing element 494.

Importantly, the two-dimensional transducer element array 402 having individually controllable transducer elements 408, 412, and 414 makes the emitted ultrasound pulse pattern variable in two-dimensions. Specifically, the two-dimensional transducer element array 402 can be controlled with respect to the position of each element within the array. By having complete control over the entire aperture, the 2-D transducer element array control system 400 allows the beam plot of the aperture to be controlled with a high degree of precision.

Figure 10:
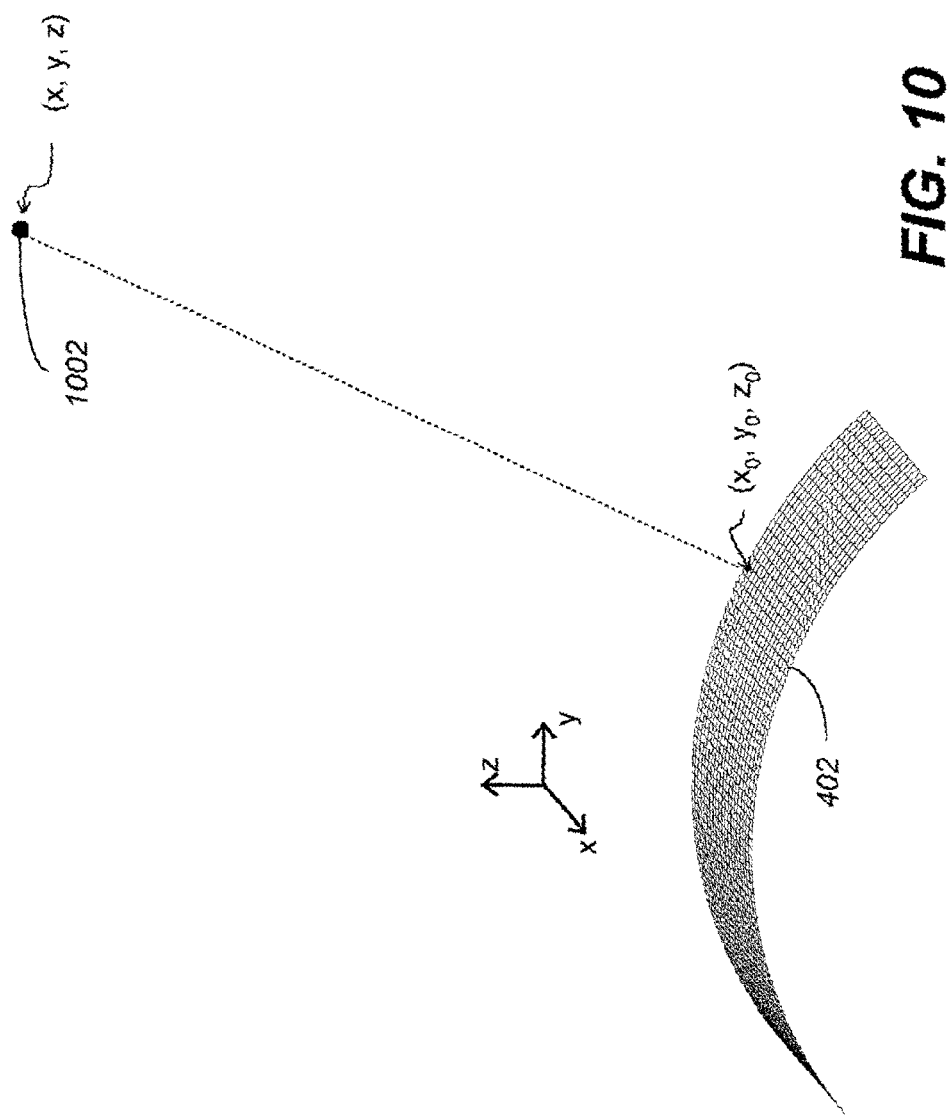
FIG. 10 is a schematic diagram illustrating an acoustic beam in both transmit and receive modes used to image a target.

Calculation of the delays used in the transmit beamformer 304 and receive beamformer 316 may be understood with reference to FIG. 10 wherein it is desired to focus the image at a target 1002, which may be, for example, some structure within the body to be imaged 30. In this case, the transmitted acoustic energy from two-dimensional transducer element array 402 is brought to a focus at target 1002 and the receive beamformer 316 focuses the received acoustic energy to maximize the receive sensitivity at target 1002. In order to transmit acoustic energy focused on target 1002, the central controller 310 may provide delay control signals to the transmit beamformer 304 for each element of the two-dimensional transducer element array 402 via connection 468 and a synchronization signal to provide a time reference for the delays. The transmit beamformer 304 causes transmit signals to be provided to each element of the two-dimensional transducer element array 402 at a beamforming delay, $T_{BF}$, after the synchronization pulse via, for example, connection 426, variable gain amplifier 422, connection 424, T/R switch 418, and connection 416. The transmit beamforming delays, $T_{BF}$, are generally different for every element of the two-dimensional transducer element array 402 and may be calculated as described below. The transmitted acoustic energy propagates to the target in a time, $T_p$, given by $$T_p = \frac{1}{v_b}\sqrt{(x-x_0)^2 + (y-y_0)^2 + (z-z_0)^2}, \quad \text{Eq. 1}$$

where, $v_b$, is the acoustic propagation velocity in the body, the two-dimensional array element is at coordinates ($x_0$, $y_0$, $z_0$), and the target 1002 is at coordinates (x, y, z). The total time, T, from the synchronization pulse to the arrival of the transmitted acoustic energy at the target 1002 may be calculated as follows:

$$T = T_{BF} + T_p. \quad \text{Eq. 2}$$

To focus the acoustic energy at the target 1002, the transmit beamforming delays, $T_{BF}$, must be chosen so that the total delays, T, are the same for every element, thus causing the ultrasonic energy from all of the two-dimensional array elements to arrive at the target 1002 simultaneously. Any set of transmit beamforming delays, $T_{BF}$, that satisfies the condition that all of the total times, T, from the synchronization pulse to the arrival of the transmitted acoustic energy from the individual elements to the target 1002 are the same is sufficient. It is clear from the above discussion that to achieve a focus at target 1002, the differences in the transmit beamforming delays, $T_{BF}$, are completely specified by the geometry.

On the receive cycle, each element of the two-dimensional transducer element array 402 receives the acoustic energy reflected from the target 1002 after a propagation delay, $T_p$, which is the same as the propagation delay for that element on transmit. To bring the target into focus, the receive beamformer 316 delays the received signal from each element by a receive beamforming delay, $T_{BF}$, that is the same as the transmit beamforming delays. As with transmit beamforming, any set of beamforming delays may be used provided the differences in beamforming delays between any two elements are correct.

Furthermore, as the time after the synchronization pulse increases, the acoustic signals arriving at the two-dimensional transducer element array 402 are due to reflections from targets at progressively deeper depths due to the finite propagation speed of the acoustic energy. The receive beamforming delays, $T_{BF}$, may be changed as a function of depth to provide receive focus at various target depths. This is referred to as dynamic receive focusing.

Interposing a protective cover 206 between the two-dimensional transducer element array 402 and the body to be imaged 30 modifies the propagation delays, $T_p$, by an amount related to the acoustic velocities of the protective cover 206, the body to be imaged 30, and to the thickness of the protective cover 206. Specifically, the protective cover 206 adds a further protective cover delay, $T_p$, given approximately by the expression:

$$T_c = h \times \left(\frac{1}{v_c} - \frac{1}{v_b}\right), \quad \text{Eq. 3}$$

where, h is the thickness of the protective cover 206 and $v_c$ is the acoustic velocity within the protective cover 206. If the protective cover 206 is made of an acoustic-matching material, then $v_c$ is approximately equal to $v_b$ and the protective cover delay, $T_c$, is approximately zero and no changes are required for the beamforming delays, $T_{BF}$. Furthermore, if the thickness, h, of the protective cover 206 is the same for all elements, then the protective cover delay, $T_c$, is the same for all transducer elements regardless of the velocity, $v_c$. Since only the differences in beamforming delays are important, it is readily seen that a protective cover 206 of uniform thickness does not change the required beamforming delays, $T_{BF}$.

Figure 12:
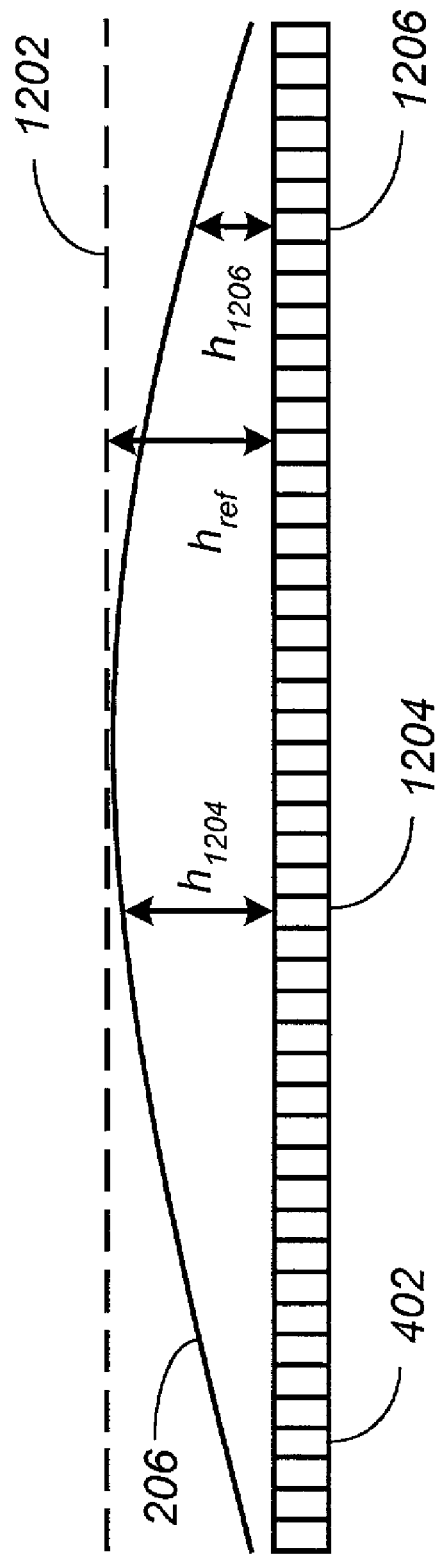
FIG. 12 is a schematic diagram illustrating the spatial relationship between the protective cover of the improved transducer of FIG. 2 and the two-dimensional transducer element array.

If, however, the thickness, h, is not uniform over the two-dimensional transducer element array 402 and the velocity, $v_c$, is different from the velocity, $v_b$, then the delay, $T_c$, will be different for every element as illustrated in FIG. 12. This will cause distortion of the wave fronts emerging from the protective cover 206 during the transmit cycle and entering the protective cover 206 during the receive cycle, resulting in loss of focus and blurring of the image. Delays used in the transmit beamformer 304 and the receive beamformer 316 can be changed from the nominal values obtained from the distance calculation so as to cancel the delay variations caused by the non-uniform thickness of the protective cover 206, thus maintaining focus and image quality. Stated another way, the new beamformer delays are equal to the beamformer delays minus the protective cover delays or $$T_{new} = T_{BF} - T_c \qquad \text{Eq. 4}$$

In the event that any of the resultant new beamformer delays is negative, a constant delay can be added to all beamformer channels to make all delays positive. For example, in FIG. 12, the two-dimensional transducer element array 402 is covered by a protective cover 206 having a non-uniform thickness such that over representative element 1204 the thickness is $h_{1204}$, and over representative element 1206 the thickness is $h_{1206}$. Then the total propagation delay from representative element 1204 to the reference plane 1202 is $$T_{1204} = \frac{h_{ref}}{v_b} + h_{1204} \times \left(\frac{1}{v_c} - \frac{1}{v_b}\right) \qquad \text{Eq. 5}$$

and the total propagation delay from representative element 1206 to the reference plane 1202 is $$T_{1206} = \frac{h_{ref}}{v_b} + h_{1206} \times \left(\frac{1}{v_c} - \frac{1}{v_b}\right). \qquad \text{Eq. 6}$$

The procedure described above for calculating beamformer delays is sufficient to produce a good focus under the most commonly encountered operating conditions. Implicit in the procedure, however, is the approximation that the variation across the aperture in the delay generated by the protective cover 206 is the same for all steering angles and focal depths.

This approximation may not be sufficiently accurate if the beam steering angle with respect to the transducer face is greater than about 45 degrees, or if the active aperture of the transducer 202 is greater than the distance to the desired focal point, or if the protective cover 206 has a thickness greater than about three wavelengths of the incident ultrasound energy, or if the protective cover 206 has areas in which the radius of curvature is less than about three times the width of the area over which it occurs.

Figure 11:
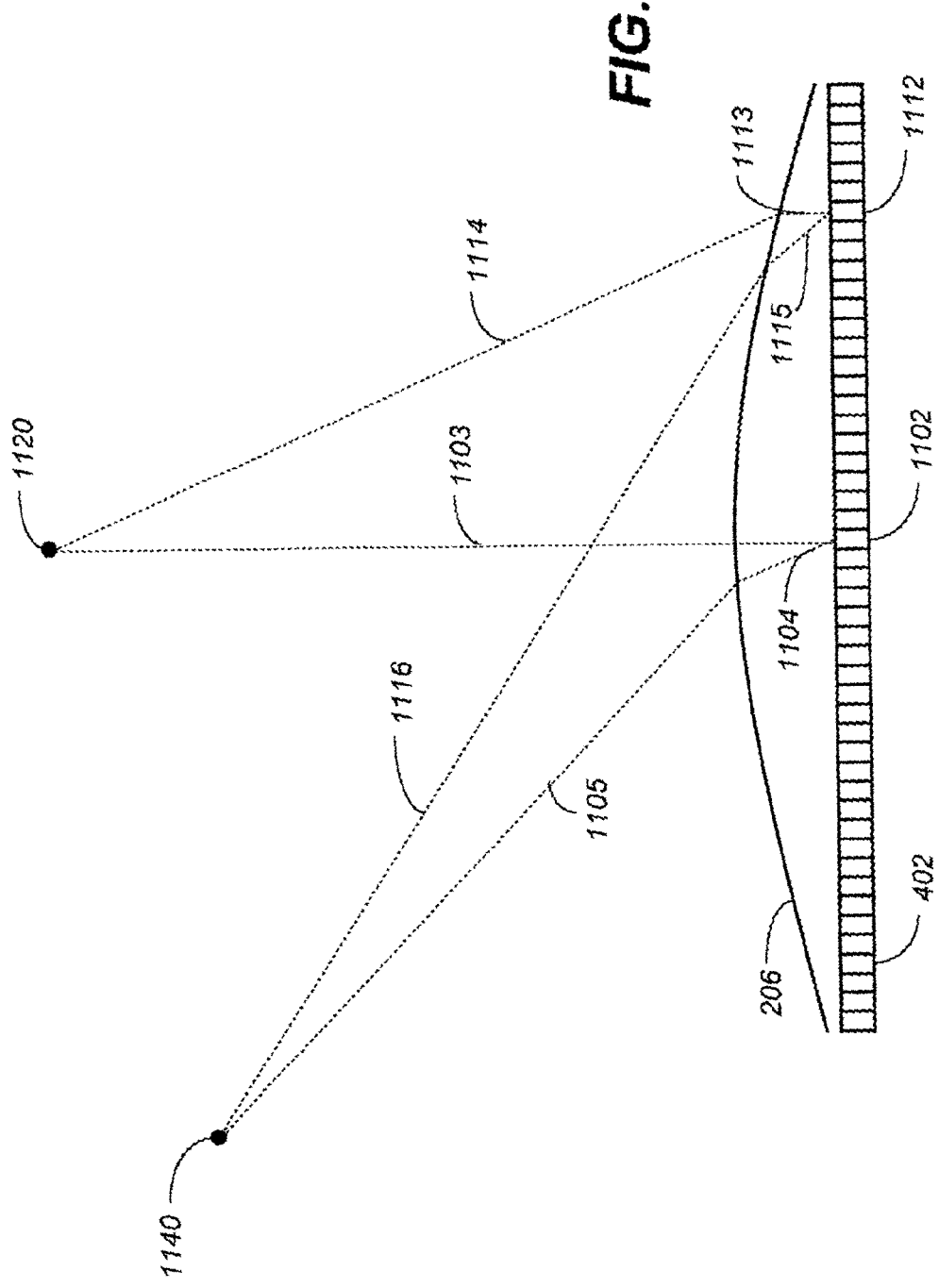
FIG. 11 is a schematic diagram illustrating multiple acoustic beams in both transmit and receive modes used to image multiple targets.

An example of this effect is illustrated in FIG. 11. In this regard, acoustic energy propagates from element 1102 to target 1120 along ray 1103, and from element 1112 to target 1120 along ray 1113 and refracted ray 1114. Acoustic energy may also propagate from element 1102 to a second target 1140 along ray 1104 and refracted ray 1105, and from element 1112 to the second target 1140 along ray 1115 and refracted ray 1116. Although the illustration is not to scale, it will be apparent that the propagation path lengths through the protective cover 206 and through the body to be imaged 30 may be different for the two different targets, and that these differences may be different for the two transducer elements 1102 and 1112. Consequently, the delays, $T_c$, through the protective cover 206 become a function not only of the element position, but also of the target position. Those skilled in the art will appreciate that the illustration presented in FIG. 11 is offered for simplicity of explanation. Individual transducer elements cannot focus by themselves. A plurality of active transducer elements acting together under the control of the image processing system 204 can be made to focus an acoustic beam that traverses the aperture.

Attention is now returned to the two-dimensional matrix of controllable transducer elements illustrated in FIG. 4. The arrangement shown in FIG. 4 allows a fully sampled, controllable, arbitrary (specified without restraint) two-dimensional delay profile to be applied to the two-dimensional transducer element array 402. Fully sampled is a term that relates to each transducer element 404, 412 and 414 being individually controlled. In preferred embodiments of such an arrangement, each individual transducer element of the two-dimensional transducer element array 402 receives some manner of control signal from the central controller 310.

The delay profile of the two-dimensional transducer element array aperture is an arbitrary, fully-sampled, controllable function of both dimensions of the aperture. The delay profile thus may be adjusted to compensate for any shape of protective cover 206, allowing the shape of the protective cover 206 to be specified to provide optimum contact with the body to be imaged 30, desirable ergonomic qualities, or other attributes as discussed previously, without degrading the image quality.

Referring now to FIGS. 5A and 5B, some preferred embodiments of transducer 202 will be described in greater detail. As depicted in FIG. 5A, transducer 202 includes a body 208 and a shaped two-dimensional transducer element array 502. As illustrated, the two-dimensional element array 502 may comprise a plurality of transducer elements 408, 412 (two identified for ease of illustration). Body 208 preferably is configured to house one or more of various components required to facilitate transmission and/or reception of acoustic energy via the two-dimensional transducer element array 502. Note that in the present illustration, the nose 210 and protective cover 206 have been removed to reveal the two-dimensional transducer element array 502. As illustrated in the partial cross-sectional side view of FIG. 5A, the two-dimensional transducer element array 502 may be cylindrically shaped. It should be appreciated that a spherically shaped two-dimensional transducer element array 502 may be selected for applications where a transducer 202 needs to remain in close contact with various surfaces of the human body as may be required.

Furthermore, body 208 may be ergonomically designed to facilitate proper positioning of the transducer 202 for performing an imaging procedure. The body 208 includes an intermediate portion 504 that is appropriately adapted to be grasped by the hand of an operator. Moreover, the body 208 may be covered by a material that not only protects the transducer electronics but has properties that make the transducer 202 easy to grasp for a sonographer.

In the embodiment depicted in FIG. 5A, body 208 contains a protective cover-mounting portion 506, which preferably flares radially in an outward fashion from an intermediate portion 504 adapted to engage protective cover 206 (not shown). At the proximal end of the transducer 202, i.e., the end opposite portion 506, a tapered or necked portion 512 is provided. Portion 512 defines an aperture for receiving electrical cordage 520. Cordage 520 is adapted to facilitate electrical communication between the transducer 202 and the image processing system 204 (not shown).

Various shapes of protective covers 206 may be utilized to protect and shield the underlying shaped two-dimensional transducer element array 502. Preferred shapes will closely cooperate with underlying two-dimensional transducer element array 502 to provide adequate acoustic coupling. Various considerations, such as the desire to promote good patient contact between the protective cover 206 and the patient, for image quality and patient comfort, as well as sonographer ease of use, for example, may make particular shapes more desirable for particular ultrasound exams. For instance, in some embodiments, the protective cover 206 can be physically configured to facilitate convenient alignment of the transducer 202 with an acoustic window of a patient. In particular, such a protective cover 206 preferably incorporates curved surfaces extending outwardly from the transducer 202. This configuration tends to facilitate convenient positioning of the protective cover 206 in relation to an acoustic window, such as an acoustic window defined by adjacent ribs of the patient. More specifically, the curved surfaces typically engage the ribs and tend to align the tissue-engagement surface with the acoustic window. As described hereinafter, the tissue-engagement surface may be provided in various configurations.

As depicted in FIG. 5B, transducer 202 includes a body 208 and a shaped two-dimensional transducer element array 552. As illustrated, the two-dimensional array 552 may comprise a plurality of transducer elements 408, 412 (two identified for ease of illustration). Here, as in the previous figure, the nose 210 and protective cover 206 have been removed to reveal the two-dimensional transducer element array 552. As illustrated in the side view of FIG. 5B, the two-dimensional transducer element array 552 may be substantially spherically shaped. A spherically shaped two-dimensional transducer element array 552 may be selected for applications where a transducer 202 needs to remain in close contact with various surfaces of the human body as may be required. It should be appreciated that two-dimensional transducer element arrays 402 having toroidal or other curved surfaces (e.g., a saddle surface) are possible and may use slightly modified beamforming than that associated with the planar two-dimensional transducer element array 402 illustrated in FIG. 4.

Reference is now directed to FIG. 6, which illustrates an improved method for ultrasound imaging with a two-dimensional transducer element arrays. In this regard, the method for ultrasound imaging 600 starts with step 602, herein designated as "Begin." The method for ultrasound imaging 600 provides a series of time delayed transmit signals to the shaped transducer as indicated in step 604 to acoustically illuminate a region of interest within a patient's body. The time delays are calculated based on the focusing geometry illustrated in FIG. 10 and any variation in delay profile resulting from propagation through the protective cover 206.

In accordance with the improved method for ultrasound imaging 600, the generated acoustic energy is propagated through a protective cover 206 that may be configured to closely mirror the shape of the two-dimensional transducer element array 502, 552, etc. as illustrated in step 606. In alternative embodiments, the two-dimensional transducer element array may be substantially planar with a superposed protective cover 206 of non-uniform thickness.

As previously described, the shape of the two-dimensional transducer element array 502, 552, may be selected based on a number of factors including patient comfort, sonographer ergonomics, the available acoustic window of the patient, as well as a host of other factors.

Next, in step 608, the received ultrasound echoes are captured and processed preferably by the same two-dimensional transducer 202 used to perform the transmit function described in steps 604 and 606. Once the received ultrasound echoes have been converted in to a voltage waveform by the transducer 202, the received echoes may be time delayed to focus the ultrasound imaging system 204 as to display desired patient structures as indicated in step 610. As in step 604, the time delays are calculated on the basis of the focusing geometry illustrated in FIG. 10 and any variation in delay profile resulting from propagation through the protective cover 206. It should be appreciated that method steps 604 through 610 may be repeated as desired to perform a diagnostic ultrasound examination. Any of a number of sonographer generated inputs may be used to terminate the method for ultrasound imaging 600 as indicated by step 612, herein labeled, "End."

As depicted in FIG. 7A, transducer 700 includes a body 702 and a protective cover 706. The protective cover 706 incorporates a generally spherical tissue-engagement surface 712, e.g., the tissue-engagement surface generally is formed as a portion of a sphere.

As shown in FIG. 7A, the tissue-engagement surface 712 or outer surface of the protective cover 206 is shaped to provide comfort to both patient and sonographer. It should be appreciated that the particular shape selected may depend on the type of exam, the size of the patient's anatomy, and/or other factors. So configured, this embodiment is capable of transmitting acoustic energy from the transducer 702 and propagating that energy along a path that is generally coextensive with, or else at some angle to a longitudinal axis 716 of the transducer 702. Preferably, a length $X_7$ of the tissue-engagement surface 712 is contacted so as to provide an appropriate cross-sectional area of engagement with a body 30 so that an adequate amount of acoustic energy can be propagated from the transducer 702 to the body 30.

As shown in FIG. 7B, the compound geometric structure of a variation of the embodiment depicted in FIG. 7A is described. More specifically, as shown in FIG. 7B, the protective cover 706 includes a tissue-engagement surface 712 that primarily is defined by a radius $R_1$ (in plan view). The surface defined by radius of curvature $R_1$ transitions at each of its ends to surfaces defined by radii of curvature $R_2$. Preferably, radii $R_2$ are defined by lengths that permit both good acoustic coupling with the patient, while maintaining a high level of comfort. While radii $R_2$ are depicted as only slightly shorter than the length of radius $R_1$ there are a host of possible relationships including the substantially spherical tissue-engagement surface formed by the external surface of the protective cover 706 as presented in FIG. 7A.

FIG. 8A illustrates an alternative embodiment of a transducer 800. The transducer 800 has a body 802 and a protective cover 806. Protective cover 806 is configured as an acoustically non-focusing protective cover 806 that substantially follows the shape of an underlying two-dimensional transducer element array (not shown). Preferably, protective cover 806 has a shaped tissue-engagement surface 812 that resembles a portion of a cylinder.

As illustrated in FIG. 8A, the transducer 802 may be configured to form a tissue engagement surface 812 having a width $X_8$ selected to facilitate propagation of acoustic energy. However, as illustrated, the width also may be selected to exploit an appropriately selected acoustic window. More specifically, if protective cover 806 is to be utilized during a thoracic acoustic-imaging procedure, for example, width $X_8$ may be selected so as to attempt to improve transducer positioning between adjacently disposed ribs, e.g., ribs 832 and 834, of the body to be imaged 30. So positioned, efficient propagation of acoustic energy from the transducer 802, between the ribs, and deeper into the body may be facilitated. As illustrated in FIG. 8A, the protective cover 806 may be substantially cylindrical in order to efficiently propagate acoustic energy through the acoustic window formed by the ribs 832 and 834.

As previously described with regard to the substantially spherical embodiment of the transducer 702 in FIG. 7B, when viewed from the side (FIG. 8B), a tissue-engagement surface 812 formed on the external surface of a protective cover 806 may be defined by a radius of curvature $R_3$. Each end of the tissue-engagement surface transitions may be defined by a radius of curvature $R_4$ that is modified in length from radius $R_3$. The protective cover 806 illustrated in FIG. 8B reveals a case where $R_4$ is less than $R_3$ So provided the tissue-engagement surface 812 presents a relatively flattened surface over the tissue-engagement area. Thus, the tissue-engagement surface 812 may be viewed as providing a near optimal propagation medium while, advantageously, attempting to exploit the geometry-limited rib access points, among others.

The external surfaces of protective covers 706 and 806, expected to form the tissue-engagement surfaces 712 and 812, generally are curved and can facilitate aligning of the tissue-engagement surface with an acoustic window. More specifically, when the tissue-engagement surface is appropriately sized, the external surfaces of the protective covers 706, 806 tend to engage the ribs, e.g., ribs 832 and 834, thereby enabling the tissue-engagement surface to nest between the ribs. Thus, the surfaces tend to align the tissue-engagement surface with the acoustic window. The curved surfaces also can enhance patient comfort during an imaging procedure, as a non-curved surface may tend to cause localized discomfort.

It should be appreciated that the protective cover covers 706 (FIG. 7B) and 806 (FIG. 8B) are exemplary only. Some embodiments of the improved transducer may call for arranging a complex protective cover and two-dimensional transducer element array 502, 522 that varies over the X, Y, and Z dimensions (see FIGS. 5A, 5B, and 10). All such variations are contemplated and within the scope of the improved ultrasound transducer.

Operation

Figure 9:
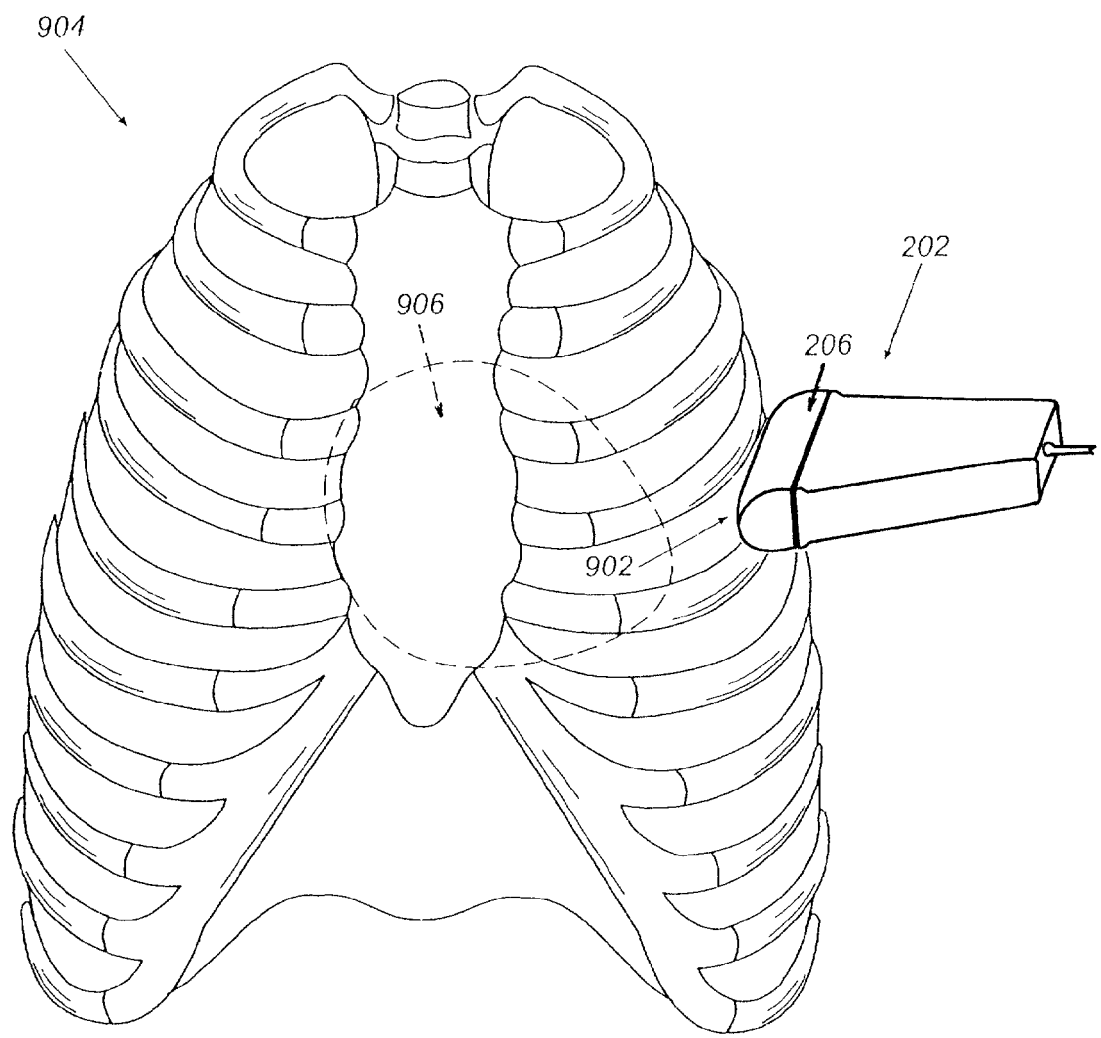
FIG. 9 is a schematic diagram depicting representative placement of the improved ultrasound transducer during a representative thoracic imaging procedure.

As depicted in FIG. 9, a preferred embodiment of the transducer 202 is shown in operative engagement with a representative acoustic window. By way of example, the transducer is appropriately positioned at an acoustic window 902 or rib access point of a representative thoracic section 904 so as to enable acoustic imaging of a heart 906, for example. As illustrated in FIG. 9, intercostal access points tend to be geometry-limited structures, i.e., the rib access points provide a bounded area through which acoustic energy may be propagated (acoustic energy is unable to penetrate bone so as to be useful for imaging). Due to the shape of protective covers 706, 806 the ability to exploit rib access points to provide acoustic imaging of tissues within the bony thorax is potentially increased. Moreover, the material(s) of the protective cover 706, 806, possessing acoustic impedance much like that of the body, tends to enhance the amount of acoustic energy propagated through a rib access point. As previously described, the acoustic energy can be electronically focused in both the lateral and elevational dimensions in both transmit and receive modes to appropriately image the structures of the heart.

It should be emphasized that the above-described embodiments of the improved ultrasound transducer, particularly, any "preferred" embodiments, are merely possible examples of implementations, merely set forth for a clear understanding of the principles of the transducer. Many variations and modifications may be made to the above-described embodiment(s) of the improved ultrasound transducer without departing substantially from the spirit and principles of the invention.

For example, although the transducer 202 has been described herein in relation to an ultrasonic imaging system 204 for use in medical applications, such as with a patient, such systems may be utilized in various other applications as well. Additionally, various surfaces associated with the protective cover 206 have been described herein as enabling convenient positioning of a transducer 202 relative to an acoustic window. In other embodiments, one or more of these surfaces may be formed as a portion of the transducer body, such as on the nose of the transducer, to provide similar functionality. All such modifications and variations are intended to be included herein within the scope of this disclosure and the present invention and protected by the following claims.

What is claimed is:

1. An acoustic imaging system, comprising:
   a transducer including a two-dimensional transducer element matrix array, the transducer having a protective cover configured to mate with a transducer body, the protective cover having a non-uniform thickness and configured to mate with a protective cover mounting portion of the transducer body, the protective cover for being superposed above the two-dimensional transducer element matrix such that acoustic energy incident at the protective cover from the two-dimensional transducer element matrix is mechanically directed by the protective cover of the non-uniform thickness, where the protective cover further comprises an acoustic material for exhibiting an acoustic impedance corresponding to an acoustic impedance of a body to be imaged and further having a shape that includes a tissue-engagement surface and curved surfaces adjacent the tissue-engagement surface, the shape specified to provide an optimum contact with the body to be imaged, wherein the curved surfaces are configured to align the tissue-engagement surface in relation to an acoustic window defined by geometry-limited access points of the body to be imaged; and
   an image processing system coupled to the transducer and configured to provide a plurality of individualized excitation signals each being delayed by a predetermined delay with respect to each other according to a two-dimensional delay profile to control respective transducer elements of the controlling lateral and elevation dimensions at different times for controlling lateral and elevation dimensions of the transmit aperture of the acoustic imaging system over time to compensate for the shape of the protective cover such that the two-dimensional transducer element matrix array generates and transmits acoustic energy through the protective cover over time such that acoustic energy transmitted through the protective cover is electrically focused according to the two-dimensional delay profile, wherein the image processing system electronically focuses transmitted acoustic energy at a target position within the body to be imaged through the protective cover as a function of (i) a position of each element of the two-dimensional transducer element array matrix, (ii) a thickness of the protective cover over a corresponding transducer element, and (iii) the target position within the body to be imaged, thereby by electrically compensating for the focusing characteristics of the protective cover as a function of non-uniform acoustic delays caused introduced by the protective cover.

2. The acoustic imaging system of claim 1, wherein at least one of the dimensions of the two-dimensional transducer element matrix array is curved.

3. The acoustic imaging system of claim 1, wherein the protective cover has an acoustic impedance of between approximately 1.3MRayl and 1.7MRayl.

4. The acoustic imaging system of claim 1, wherein the protective cover has a transducer-engagement end having the tissue-engagement surface, the transducer-engagement end being configured to engage a transducer body, the tissue engagement surface forming a portion of a substantially cylindrical surface.

5. The acoustic imaging system of claim 1, wherein the tissue engagement surface forms a portion of a substantially spherical surface.

6. The acoustic imaging system of claim 1, wherein the transducer body is ergonomically adapted to be grasped by the hand of an operator.

7. The acoustic imaging system of claim 1, wherein the image processing system receives a plurality of individualized receive mode signals from a plurality of transducer elements, the receive mode signals representative of the incident acoustic energy at a plurality of the transducer elements of the two-dimensional transducer element matrix array that traverses the protective cover.

8. A method for acoustically imaging a patient, comprising the acts of:
providing a transducer having a two-dimensional transducer element matrix array encased by a protective cover and a transducer body, the protective cover having a non-uniform thickness and configured to mate with a protective cover mounting portion of the transducer body, the protective cover for being superposed above the two-dimensional transducer element matrix such that acoustic energy transmitted form the protective cover and into the body is mechanically directed by the protective cover of the non-uniform thickness, wherein the two-dimensional transducer element matrix array and the protective cover are shaped to reduce patient discomfort, further wherein the protective cover further comprises an acoustic material for exhibiting an acoustic impedance corresponding to an acoustic impedance of a body to be imaged and further having a shape that includes a tissue-engagement surface and curved surfaces adjacent the tissue-engagement surface, the shape specified to provide an optimum contact with the body to be imaged, wherein the curved surfaces are configured to align the tissue-engagement surface in relation to an acoustic window defined by geometry-limited access points of the body to be imaged;
generating a plurality of time delayed transmit signals each for separately controlling a respective transducer element of the two-dimensional transducer element matrix array to electronically focus acoustic transmit waves that traverse through the protective cover, the plurality of time delayed transmit signals each being delayed by a predetermined delay with respect to each other according to a two-dimensional delay profile to control respective transducer elements of the plurality of transducer elements at different times for controlling lateral and elevation dimensions of a transmit aperture over time to compensate for the shape of the protective cover such that the two-dimensional transducer element matrix array generates and transmits acoustic energy through the protective cover over time according to the two-dimensional delay profile; and
receiving a plurality of time delayed response echoes at the separately controllable individual transducer elements of the two-dimensional transducer element matrix array to electrically focus acoustic receive echoes that traverse the protective cover, wherein the image processing system electronically focuses transmitted acoustic energy at a target position within the body to be imaged through the protective cover as a function of (i) a position of each element of the two-dimensional transducer element array matrix, (ii) a thickness of the protective cover over a corresponding transducer element, and (iii) the target position within the body to be imaged, thereby by electronically compensating for the focusing characteristics of the protective cover as a function of non-uniform acoustic delays caused introduced by the protective cover.

9. The method of claim 8, further comprising the act of: processing the reflected acoustic echoes to generate an image.

10. The method of claim 8, further comprises the acts of:
accessing the acoustic window of a patient; and
transmitting acoustic energy through the protective cover and into the patient via the acoustic window.

11. The method of claim 10, wherein the act of accessing the acoustic window comprises an acoustic window formed between adjacently disposed ribs of the patient.

* * * * *